United States Patent
Lamarque et al.

(10) Patent No.: US 10,264,954 B2
(45) Date of Patent: Apr. 23, 2019

(54) STRUCTURED THREE-DIMENSIONAL IMAGING DEVICE WITH REVERSIBLE IMAGE GUIDES

(71) Applicants: Universite Technologie de Compiegne—UTC, Compiegne (FR); Centre National de la Recherche Scientifique (CNRS), Paris (FR); Institut National des Sciences Appliquees de Lyon, Villeurbanne (FR); Ecole Centrale de Lyon, Ecully (FR); Universite Claude Bernard Lyon 1, Villeurbanne (FR)

(72) Inventors: Frederic Lamarque, Compiegne (FR); Erwan Dupont, Tracy le Val (FR); Christine Prelle, Compiegne (FR); Laurent Petit, Margny les Compiegne (FR); Tanneguy Redarce, Bron (FR)

(73) Assignees: UNIVERSITE TECHNOLOGIE DE COMPIEGNE—UTC, Compiegne (FR); CENTRE NATIONAL DE LA RECHERCHE SCIENTIFIQUE (CNRS), Paris (FR); INSTITUT NATIONAL DES SCIENCES APPLIQUEES DE LYON, Ecully (FR); ECOLE CENTRALE DE LYON, Villeubanne (FR); UNIVERSITE CLAUDE BERNARD LYON 1, Villeubanne (FR)

( * ) Notice: Subject to any disclaimer, the term of this patent is extended or adjusted under 35 U.S.C. 154(b) by 0 days.

(21) Appl. No.: 15/105,528

(22) PCT Filed: Dec. 17, 2014

(86) PCT No.: PCT/EP2014/078197
§ 371 (c)(1),
(2) Date: Jun. 16, 2016

(87) PCT Pub. No.: WO2015/091631
PCT Pub. Date: Jun. 25, 2015

(65) Prior Publication Data
US 2016/0316999 A1    Nov. 3, 2016

(30) Foreign Application Priority Data
Dec. 17, 2013   (FR) .................................. 13 62746

(51) Int. Cl.
*A61B 1/00*       (2006.01)
*A61B 1/002*      (2006.01)
(Continued)

(52) U.S. Cl.
CPC .......... *A61B 1/00193* (2013.01); *A61B 1/002* (2013.01); *A61B 1/0017* (2013.01);
(Continued)

(58) Field of Classification Search
CPC ............ A61B 1/00096; A61B 1/00114; A61B 1/00117; A61B 1/00124; A61B 1/00126;
(Continued)

(56) References Cited

U.S. PATENT DOCUMENTS 4,862,873 A  *  9/1989  Yajima ............... A61B 1/00193
                                                              348/45
2005/0222500 A1*  10/2005  Itoi ..................... A61B 1/0005
                                                              600/180

FOREIGN PATENT DOCUMENTS

DE           3818104 A1    12/1988
WO       WO 9413189 A1     6/1994
(Continued)

OTHER PUBLICATIONS

Search Report and Written Opinion of the ISA in PCT/EP2014/078197 dated Mar. 17, 2015, with English translation coversheet. 12 pages.

(Continued)

*Primary Examiner* — Ryan Henderson
(74) *Attorney, Agent, or Firm* — Womble Bond Dickinson (US) LLP

(57) ABSTRACT

The invention relates to an imaging device (E) comprising: at least one generator (1) of structured light; an emission first image guide (5, 5') for uplinking the structured light from the generator (1) to an object to be observed; and a return second image guide (5', 5) for downlinking the light reflected by said object to be observed to a system (2) for capturing said reflected light. Each of the two image guides (5, 5') is able to uplink the structured light and downlink the reflected light, and the imaging device comprises an optical switch (3) configurable into three different operating modes.

15 Claims, 10 Drawing Sheets

(51) Int. Cl.

| | |
|---|---|
| *A61B 1/06* | (2006.01) |
| *A61B 1/07* | (2006.01) |
| *G02B 27/22* | (2018.01) |
| *G02B 27/24* | (2006.01) |
| *G02B 27/26* | (2006.01) |
| *G02B 6/04* | (2006.01) |
| *G02B 6/06* | (2006.01) |
| *H04N 13/00* | (2018.01) |
| *H04N 13/20* | (2018.01) |
| *G02B 23/24* | (2006.01) |
| *G02B 23/26* | (2006.01) |
| *G02B 6/35* | (2006.01) |
| *H04N 5/232* | (2006.01) |

(52) U.S. Cl.
CPC ...... *A61B 1/00163* (2013.01); *A61B 1/00165* (2013.01); *A61B 1/00167* (2013.01); *A61B 1/0669* (2013.01); *A61B 1/07* (2013.01); *G02B 6/04* (2013.01); *G02B 6/06* (2013.01); *G02B 6/3514* (2013.01); *G02B 23/2415* (2013.01); *G02B 23/2423* (2013.01); *G02B 23/2469* (2013.01); *G02B 23/26* (2013.01); *G02B 27/22* (2013.01); *G02B 27/24* (2013.01); *G02B 27/26* (2013.01); *H04N 5/23245* (2013.01); *H04N 13/00* (2013.01); *H04N 13/20* (2018.05)

(58) Field of Classification Search
CPC ............ A61B 1/00163; A61B 1/00165; A61B 1/00167; A61B 1/0017; A61B 1/00172; A61B 1/00174; A61B 1/00177; A61B 1/00179; A61B 1/00181; A61B 1/00183; A61B 1/00186; A61B 1/00188; A61B 1/0019; A61B 1/00193; A61B 1/00195; A61B 1/00197; A61B 1/002; A61B 1/04; A61B 1/042; A61B 1/045; A61B 1/05; A61B 1/051053; A61B 1/055; A61B 6/022; G02B 6/04; G02B 6/06; G02B 6/065; G02B 27/22; G02B 27/24; G02B 27/26; H04N 13/00; H04N 13/02; H04N 2013/00

See application file for complete search history.

(56) References Cited

FOREIGN PATENT DOCUMENTS

| WO | WO 0003272 A2 | 1/2000 |
|---|---|---|
| WO | WO 2011014687 A2 | 2/2011 |
| WO | WO 2012076128 A1 | 6/2012 |
| WO | WO 2013033811 A1 | 3/2013 |

OTHER PUBLICATIONS

Search Report in French Application No. 1362746 dated Jul. 31, 2014, with English translation coversheet. 8 pages.

\* cited by examiner

STRUCTURED THREE-DIMENSIONAL IMAGING DEVICE WITH REVERSIBLE IMAGE GUIDES

GENERAL FIELD

The invention relates to a three-dimensional imaging device.

PRIOR ART

Image devices having three-dimensional vision are used in many fields, one of these fields being that of endoscopy.

Endoscopy is a medical or industrial exploration and imaging process which views the interior of conduits or cavities inaccessible to the eye.

Endoscopy can especially be used either for diagnostics or to treat a medical condition, by colonoscopy for example.

In general, endoscopy is performed bidimensionally; but there are endoscopes having three-dimensional vision. There are different processes of acquisition of images for obtaining a three-dimensional measurement of an object by means of an endoscope. Of known methods, some function by vision known as "passive". According to these methods, two offset images of the object are acquired simultaneously by two separate ways to reproduce a perception of the relief.

Another type of known method consists of implementing vision known as "active" by means of projection of a structured light. A light is called structured when it is spatially modulated in intensity. It consists of in space a light pattern such as fringes, a grill or other more complex shapes.

Projection of structured light is particularly useful for acquiring dimensional information concerning an object to be observed. Scanning this object with a structured light and acquiring the deformations of the reflected light at a determined angle enable the three-dimensional geometry of the object to be deduced.

Scanning the object is done according to various processes, especially by temporary modification of the content of the projected structured light. Temporary modification of the structured light consists of spatially illuminating the surface of the object to be observed with a determined pattern, then modifying the pattern over time. For example, during acquisition, a first pattern with horizontal fringes and a second pattern of vertical fringes orthogonal to the fringes of the first pattern are successively generated and projected.

At the same time, an acquisition system receives the images consisting of the light reflected by the object to be observed and can then reconstitute the surface in three dimensions of said object, by way of analysis of these images and a reconstruction algorithm (for example an algorithm of phase offset type).

Some known endoscopes with active vision comprise optoelectronic components such as a camera or a generator of structured light at their distal end.

Now, an endoscope must have a small enough diameter so it can be inserted into a conduit or a narrow cavity. The designing of such endoscopes with active vision therefore generally involves the search for miniaturization of these optoelectronic components to minimize the diameter of the endoscope.

But, this search for miniaturization in turn implies a limitation to the optical performance of the endoscope (for example, in terms of resolution) and/or increase in its manufacturing cost.

Also, the majority of endoscopes of known type does not reconstruct some portions of three-dimensional objects of complex relief when the endoscope is placed in a determined position, especially the many endoscopes projecting structured light according to a single angle of incidence. On the one hand, areas such as cavities can remain unlit by the endoscope. On the other hand, unwanted specular reflections can parasite the structured image reflected towards the endoscope.

PRESENTATION OF THE INVENTION

The aim of the invention is to image surfaces of complex relief to be observed and reduce the miniaturization restrictions imposed on the used device.

Another aim of the invention is to boost the quantity of information representative of an object observed by an imaging device.

In this respect and according to a first aspect, an imaging device is proposed comprising:
  at least one generator of structured light,
  a first emission image guide for conveying by uplink the structured light from the generator towards an object to be observed,
  a second return image guide for conveying by downlink the light reflected by said object to be observed as far as an acquisition system of said reflected light,
wherein each of the two image guides is capable of conveying the structured light by uplink and the reflected light by downlink. The device comprises an optical switch that can be configured into:
  a first mode in which it selectively directs the structured light coming from the generator towards the first image guide, by uplink, and at the same time selectively directs the light reflected by the object from the second image guide, by downlink, as far as the acquisition system,
  a second mode in which it selectively directs the structured light coming from the generator towards the second image guide, by uplink, and at the same time selectively directs the light reflected by the object from the first image guide, by downlink, as far as the acquisition system, and
  a third mode in which it simultaneously directs light originating from the two image guides, by downlink, as far as the acquisition system.

The first and second modes of such a device are two alternative active vision modes, and produce different visual information on an object observed of a complex three-dimensional envelope. In fact, the areas of the observed object onto which the structured light is reflected when the first image guide is used uplink (first active vision mode), and when the second image guide is used uplink (second active vision mode) are not necessarily identical.

The third mode of the device is a passive stereovision mode for acquisition of three-dimensional information complementary to those acquired by means of the two active embodiments.

In this way, because of the three modes in which the optical switch can be configured, a larger amount of visual information can be collected with only two image guides, enabling the envelope of the object to be reconstructed in three dimensions.

The device according to this first aspect of the invention can also comprise the following characteristics, taken singly or else in combination when this is technically possible.

The device comprises a secondary light source adapted to illuminate the object.

The device comprises an optical fiber for conveying light emitted by the secondary source towards the object.

The device comprises a distal tip configured to diffuse light conveyed by each of the two image guides on the object to be observed and redirect towards each of the two image guides light reflected by said object.

The device comprises two distal arms, each distal arm being configured to diffuse the light conveyed by one of the image guides and redirect towards this image guide the light reflected by said object, the two arms being movable relative to each other so as to form a variable angle of reflection with the object to be observed as a function of the distance of the object relative to the two arms.

Each image guide comprises a bundle of optical fibers.

Each image guide comprises an array of mirrors and/or lenses.

The optical switch comprises a primary mirror positioned between the generator and the two image guides, the primary mirror being adapted to enable selective redirection of structured light originating from the generator towards a first optical axis leading to the first image guide or towards a second optical axis leading to the second image guide.

The generator is configured to emit structured light along the first axis leading to the first image guide, and the primary mirror is movable between:
- an active position in which the primary mirror cuts the first axis between the generator and the first image guide and reorients towards the second image guide the structured light originating from the generator along the second axis, and
- a passive position in which the primary mirror does not cut the first axe.

The optical switch comprises another mirror arranged to redirect the light reflected by the primary mirror when it is positioned in its active position, on another axis parallel to the first axis, the first guide having a proximal opening aligned with the first axis, and the second guide having a proximal opening aligned with the other axe.

The optical switch comprises a first secondary mirror, a second secondary mirror, and the first secondary mirror is movable between:
- an active position in which the first secondary mirror cuts the first axis between the generator and the first image guide, and reorients towards a camera light emanating from the first image guide, and
- a passive position in which the first secondary mirror does not cut the first axe.

In addition, the second secondary mirror is movable between:
- an active position in which the second secondary mirror cuts the second axis between the generator and the primary mirror, and reorients towards the acquisition system light emanating from the second image guide, and
- a passive position in which the first secondary mirror does not cut the first axe.

The optical switch further comprises a control unit adapted to:
- in the first embodiment, position the primary mirror and the first secondary mirror in a passive position and the second secondary mirror in an active position, and
- in the second embodiment, position the primary mirror and the first secondary mirror in an active position and the second secondary mirror in a passive position,
- in the third embodiment, position the secondary mirrors in an active position.

The primary mirror and the secondary mirrors are each translationally movable by means of at least one bistable electromagnetic actuator.

The acquisition system comprises two cameras, each camera being arranged to receive light coming from one of the two image guides.

The device can be an endoscope.

The invention proposes according to a second aspect an imaging method comprising the following steps:
- generating structured light,
- conveying in a first image guide by uplink the structured light generated towards an object to be observed,
- conveying in a second image guide by downlink the light reflected by said object to be observed as far as an acquisition system of said reflected light,
- acquiring the reflected light by means of the acquisition system, the method being characterized by the following steps, each of the two image guides being capable of conveying the structured light by uplink and the reflected light by downlink:
- selectively directing the structured light generated towards the first image guide, by uplink, and at the same time selectively directing the light reflected by the object from the second image guide, by downlink, as far as the acquisition system,
- selectively directing the structured light generated towards the second image guide, by uplink, and at the same time selectively directing the light reflected by the object from the first image guide, by downlink, as far as the acquisition system, and
- simultaneously directing light originating from the two image guides by downlink as far as the acquisition system.

The invention proposes according to a third aspect an imaging device, such as an endoscope, comprising:
- at least one generator of structured light,
- a first image emission guide for conveying by uplink the structured light from the generator as far as a distal tip for emitting the conveyed structured light to an object to be observed,
- a second return image guide for conveying by downlink the light reflected by said object to be observed as far as an acquisition system of said reflected light, wherein each of the two image guides is capable of conveying the structured light by uplink and the reflected light by downlink, the device further comprising an optical switch for:
- selectively directing the structured light coming from the generation means by uplink towards one of the two image guides and
- at the same time selectively directing the light reflected by the object to be observed from the other of the two image guides, by downlink, as far as the acquisition means.

The device according to this third aspect can also comprise the optional characteristics of the device according to the first aspect of the invention.

DESCRIPTION OF FIGURES

Other characteristics, aims and advantages of the invention will emerge from the following description which is purely illustrative and non-limiting and which must be considered in terms of the appended drawings, wherein.

In all figures, similar elements bear identical reference numerals.

DETAILED DESCRIPTION OF THE INVENTION

Figure 1:
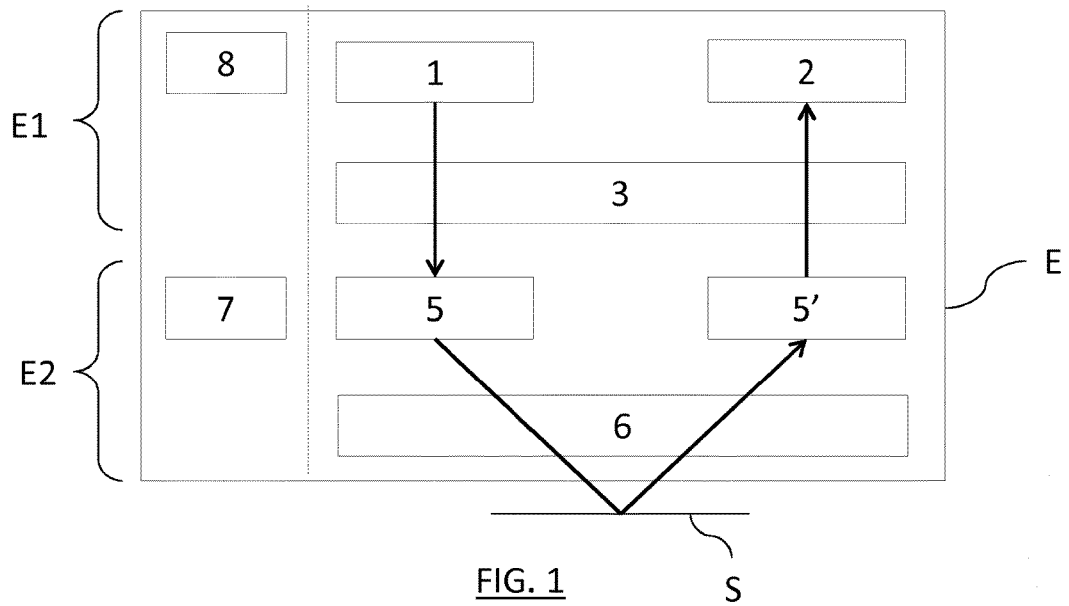
FIG. 1 schematically illustrates an imaging device according to a first embodiment, configured in a first mode.

In reference to FIG. 1, an imaging device E comprises at least one generator 1 of structured light, an optical acquisition system 2, an optical switch 3, and two image guides 5 and 5'.

The imaging device E comprises a proximal part E1 comprising various optoelectronic devices, and a distal part E2.

The proximal part E1 comprises the generator 1 of structured light, the optical acquisition system 2 and the optical switch 3.

The distal part E2 comprises the two image guides 5 and 5', each image guide being adapted to convey structured light.

The distal part E2 terminates by at least one distal tip 6 intended to be placed facing the surface S of a three-dimensional object to be analyzed.

Several types of optical paths are distinguished in the endoscope. "Uplink" conventionally means any optical path conveying light from the proximal part E1 towards the distal part E2, and by contrast "downlink" means any optical path conveying light from the distal part E2 towards the proximal part E1.

Each image guide 5, 5' is adapted to convey structured light emitted by the generator 1 by uplink up to the distal tip 6 and also to convey light reflected by an observed object, by downlink, down to the acquisition system.

In other words, each image guide consists of a flexible or rigid optical interface for transmitting an image from one of its ends to its other end.

The optical switch 3 ensures an optical interface function between both the generator and the acquisition system and the image guides 5 and 5'. The optical switch 3 is adapted to:
  selectively direct structured light generated by the generator towards one of the two image guides by uplink, and
  at the same time selectively direct light reflected by the object to be observed from the other of the two image guides, by downlink, towards the acquisition system 2.

The imaging device E further comprises a secondary light source 8 and an optical fiber 7 attached to the secondary light source 8 and to the distal tip 6. The optical fiber 7 is separate from the image guides 5 and 5'.

The light source 8 is adapted to emit structured or non-structured light. The case where the light source 8 emits non-structured light will be used as an example hereinbelow.

Figure 2:
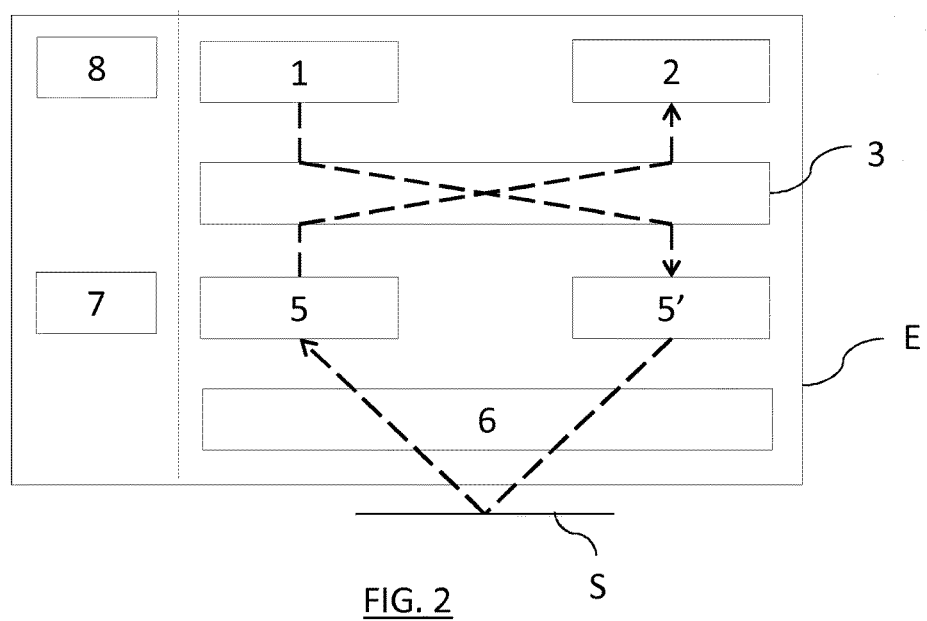
FIG. 2 schematically illustrates the device of FIG. 1, configured in a second mode.
Figure 3:
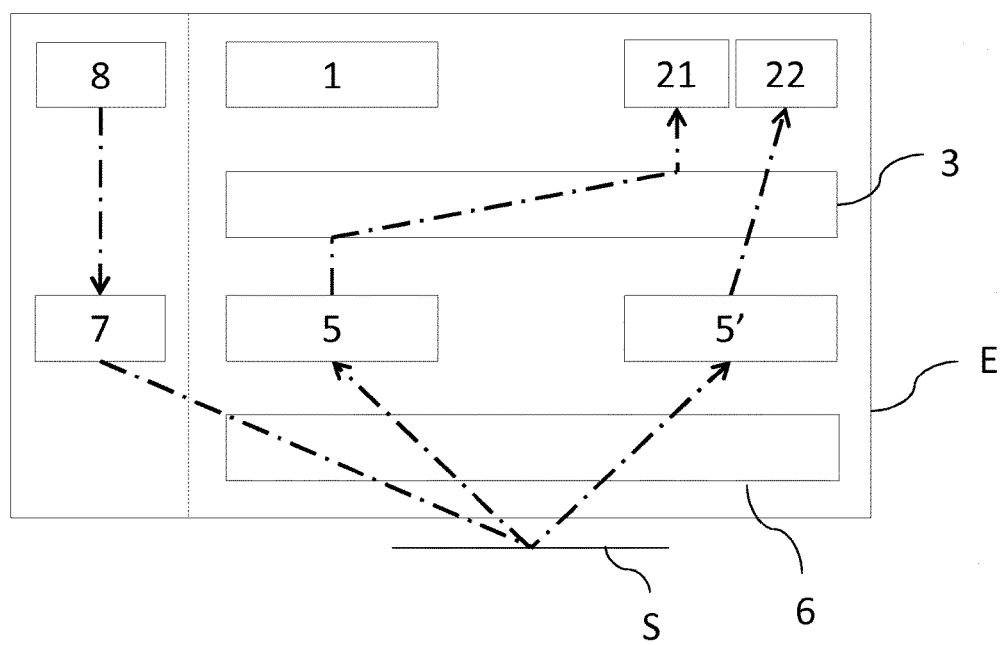
FIG. 3 schematically illustrates the imaging device of FIG. 1, configured in a third mode.

Three modes of the imaging device E are illustrated in FIGS. 1 to 3.

In a first mode shown in FIG. 1, so-called left active vision mode, the optical switch 3 is configured to direct structured light generated by the generator 1 selectively towards the first image guide 5, and is configured at the same time to redirect light originating from the second image guide 5' towards the acquisition system 2.

In this way, in the left active vision mode, structured light (shown by solid arrows) generated by the generator 1 is directed by the optical switch 3 selectively towards the first image guide 5. The structured light spreads in the guide 5 as far as the distal tip 6, exits from the imaging device E by the distal tip 6 and is reflected in an area of the surface S of a three-dimensional object to be observed. The structured light reflected in this way enters the device E by the distal tip, spreads by downlink into the second image guide 5' not used uplink, then is switched by the optical switch 3 towards the acquisition system 2.

In a second mode illustrated in FIG. 2, so-called right active vision mode, the optical switch 3 is configured to direct structured light generated by the generator 1 selectively towards the first image guide 5', and is configured at the same time to redirect light originating from the second image guide 5 towards the acquisition system 2.

In this way, in the right active vision mode, structured light (shown by dotted arrows) generated by the generator 1 is directed by the optical switch 3 selectively towards the second image guide 5'. The structured light spreads in the second guide 5' as far as the distal tip 6, exits from the imaging device E by the distal tip 6 and is reflected in an area of the surface S of the three-dimensional object to be observed. The structured light reflected in this way enters the imaging device E by the distal tip, spreads by downlink in the first image guide 5 not used uplink, then is switched by the optical switch 3 towards the acquisition system 2.

In a third mode illustrated in FIG. 3, so-called passive stereovision mode, the optical switch 3 is configured to direct structured or non-structured light originating from the two image guides 5 and 5' towards the acquisition system 2.

In this way, in the passive stereovision mode, light (shown by dash-dot arrows) generated by the secondary light source 8 spreads in the optical fiber 7 up to the distal tip 6, exits from the imaging device E by the distal tip 6 and is reflected in an area of the surface S of a three-dimensional object to be observed. The light reflected in this way again enters the imaging device by the distal tip 6, spreads by downlink in the two image guides 5 and 5' not used uplink, then is switched by the optical switch 3 towards the acquisition system 2.

In the passive stereovision mode, the additional optical fiber 7 is used uplink while the two image guides 5, 5' are used downlink.

The imaging device E can therefore fluctuate from one embodiment to another by simple reconfiguration of the optical switch 3. No optoelectronic device is used in the distal tip 6, the switching being in the proximal part E1 of the imaging device E. In particular no scanning device of galvanometric mirror type, or piezoelectric or electromagnetic actuator is required in the distal tip which is fixed and not supplied electrically.

The passive stereovision mode captures clouds of denser points under some conditions (if the aim is to measure in real time, the active vision cannot easily reconstruct dense clouds of points, contrary to passive stereovision). Passive stereovision also benefits from sharp lighting and therefore does not undergo the same specular effects as active vision (possibility of reconstructing specular areas which posed a problem in active vision). Also, some surfaces absorbing light poorly diffuse patterns in active vision; passive stereovision in this case provides images of better quality.

However, on united surfaces, active vision provides better results than passive stereovision.

The proposed imaging device E produces good-quality images for surfaces to be inspected of very different reliefs.

In the following, a first embodiment will be considered in which the imaging device E is an endoscope, given that the invention is not limited to this particularly advantageous application.

In this application to the field of the endoscopy, the distal part of the endoscope E is intended to be inserted into the body of a patient non-invasively.

First Embodiment of Distal Part

In this first embodiment, the distal part E2 comprises an external tubular sheath defining an internal conduit. The image guides 5 and 5' are housed in the internal conduit and extend between the distal tip 6 and the optical switch 3 of the proximal part E1.

Each image guide 5, 5' comprises for example a core comprising a bundle of parallel optical fibers, each fiber corresponding to a specific pixel of an image to be conveyed. The many optical fibers are enclosed by a sheath of silica and a flexible protective coating, made of plastic for example.

The number and diameter of the optical fibers of each optical guide depend on the preferred image resolution. Typically, an image guide comprises at least 50,000 optical fibers, for example 70,000; the diameter of each optical fiber is comprised between 1 and 5 micrometers, for example 3.5 micrometers, and the diameter of the image guide in its entirety is comprised between 1 and 2 millimeters, for example 1.3 millimeter.

Of course, the image guides with optical fibers presented above can be replaced by other types of image guides for transmitting an image from one of their ends to their other end.

Figure 4:
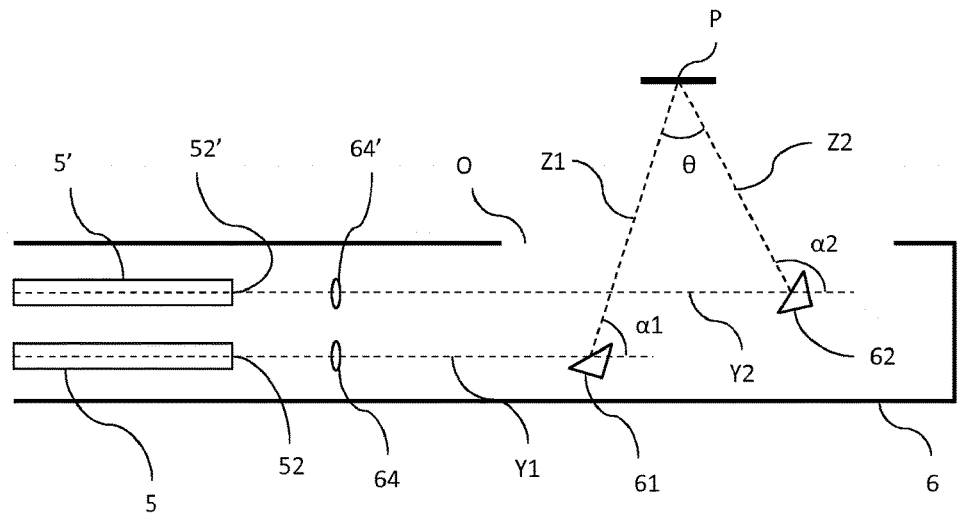
FIG. 4 is a first view in partial section of a distal part of an imaging device.

An embodiment of distal tip 6 is illustrated in FIG. 4.

The tip 6 is a hollow body extending along a longitudinal direction, and comprises a lateral optical opening O. This optical opening O can for example be covered by a transparent surface. Arranging the optical opening O laterally increases the angle θ (angle of triangulation) and therefore improves the resolution of axial measurement.

The two image guides 5 and 5' each comprise a distal opening 52, 52' attached to the distal tip 6.

Arranged inside the tip 6 and facing the lateral opening O are two reflecting optical elements 61 and 62, for example mirrors comprising a reflecting planar surface.

A first reflecting optical element 61 is placed facing the distal opening 52 of the first image guide 5, which is centered on a first optical axis Y1 of longitudinal direction.

The first reflecting optical element 61 is arranged so as to reflect incident structured light according to the longitudinal axis Y1 coming from the distal opening 52, and redirect it along a transversal axis Z1 forming an angle α1 comprised between 45 and 90° relative to the longitudinal axis, for example 60°.

Also, a second reflecting optical element 62 is placed facing the distal opening 52' of the second image guide 5', which is centered on a second optical axis Y2 also of longitudinal direction.

The second reflecting optical element 62 is arranged so as to reflect incident structured light according to the longitudinal axis Y2 coming from the distal opening 52', and redirect it along a transversal axis Z2 forming an angle α2 between 90° and 135° relative to the longitudinal axis, for example 110°.

The respective positions of the reflecting optical elements 61 and 62 along their longitudinal axes and their respective angles of redirection α1, α2 are selected so that the transversal axes Z1, Z2 of these reflecting optical elements 61, 62 pass through the transversal opening O and cross at least at one observation point P located outside the tip 6 beyond the transversal opening.

In this way, when the observation point P encounters the surface S of a three-dimensional object, light redirected by one of the elements optical (for example 61) is reflected at least partially at this observation point P, and is returned to the other of the optical elements (for example 62).

Advantageously, the angle between the transversal axes Z1 and Z2 is comprised between 50° and 70°, for example 60°, a range of angles particularly adapted to perform stereoscopy according to a particular configuration of the endoscope which will be detailed later in this description. This range of angle offers a good compromise between axial resolution (which increases the value of this angle) and the dimension of the measurable area (especially if the observation point P is located on a surface not parallel to the opening O).

At least one lens 64 can be placed between the distal opening 52 of the first image guide 5 and the reflecting optical element 61. Similarly, at least one lens 64' can be placed between the distal opening 52' of the second image guide 5' and the optical element 62. Each lens 64, 64' serves to focus a light beam coming from the facing distal opening 52, 52' towards the observation point P, and focus a beam reflected onto the point P towards the facing opening distal 52, 52'. Each lens can be combined with a diaphragm which regulates the depth of field (i.e., the area of sharpness in front of and behind the point P).

The distance between the lens 64 (respectively 64') and the opening 52 (respectively 52') depends on the focal point of the lens and the distance between the interface 52 (respectively 52') and the point P.

The resulting tip 6 is electrically and thermally inert. Its average radius relative to the longitudinal axis can therefore be reduced to low cost, as no electronic device is required and needs to be miniaturized.

Figure 5:
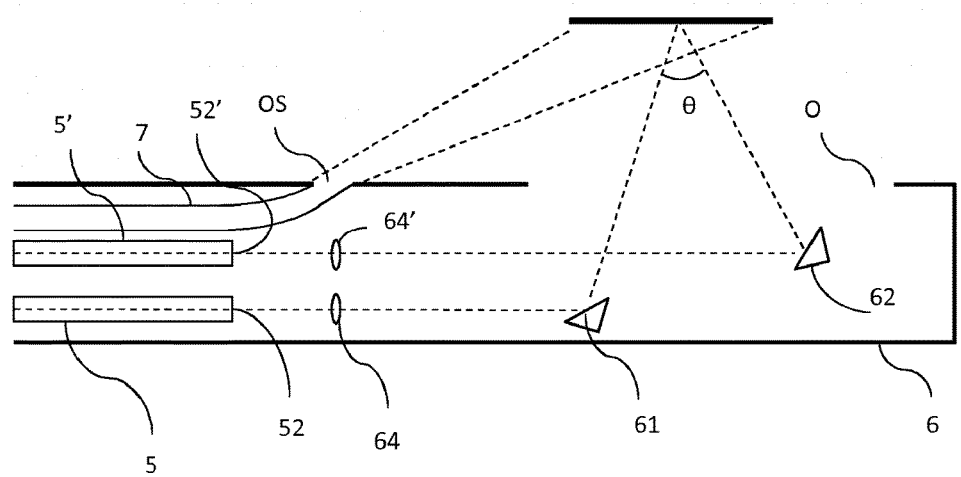
FIG. 5 is a second view in partial section of the distal part according to a second embodiment.

In reference to FIG. 5, the tip 6 also comprises a secondary lateral optical opening OS separate to the opening O. The lateral opening O and the secondary lateral opening OS can for example be centered on the same generator of the external surface of a tip 6 of cylindrical shape, the secondary opening OS being made at a proximal position relative to the opening O. The optical fiber 7 is attached to the secondary opening OS.

The secondary opening OS is configured to emit light not focused on an area of an object facing the opening O, the lit area encompassing the area on which structured light emanating from one or the other of the optical elements 61 or 62 is reflected.

First Embodiment of Proximal Part

Figure 6:
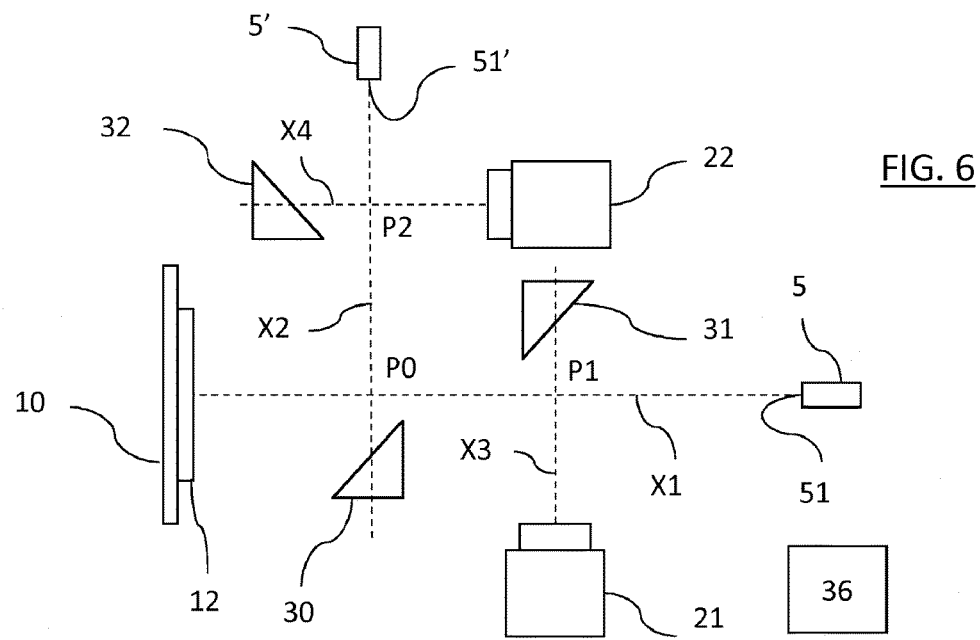
FIG. 6 partially illustrates the proximal part of an imaging device, according to an embodiment.

In reference to FIG. 6, the image guide 5 (respectively 5') comprises a proximal opening 51 (respectively 51') attached to the proximal part E1 of the endoscope E and opposite the distal opening 52 (respectively 52').

The generator 1 of structured light comprises a source 10 of monochromatic white light, coherent or incoherent, and a matrix 12 of micro-mirrors.

The matrix 12 of micro-mirrors is an electromechanical system usually used in video projectors comprising a large number of micro-mirrors and enabling projection of an image by reflection of the light onto each of the micro-mirrors. Each micro-mirror of the matrix 12 can assume two positions: one position in which it reflects light emitted by the source 10 onto an optical path and one position in which it reflects light emitted by the source towards an absorbent surface. In this way, the matrix of micro-mirrors generates a pattern of structured light from light emitted by the source, the pattern depending on the respective positions of the micro-mirrors. Also, modification of the pattern on an object to be observed can be done without modification of optical regulation of conjugation of the matrix of micro-mirrors and the image guides. It also produces very good resolution and considerable flexibility for generating complex encodings of the structured light, for example dynamically (at a frequency which can be over 100 Hz).

The generator 1 can comprise, in place of a matrix of micro-mirrors 12, a diffractive optics component (passive optics) or a network of liquid crystals (controlled actively).

In general, the generator 1 is adapted to emit a plurality of light beams in the main direction of a first axis X1. One or more lenses (not shown) can be placed for this purpose at the outlet of the matrix of micro-mirrors.

In the proximal part E1, the proximal opening 51 of the first image guide 5 is centered on the first optical axis X1, facing the matrix 12. The proximal opening 51' of the second image guide 5' is also centered on a second optical axis X2 crossing the first optical axis X1 at a point P0. In the embodiment illustrated, the first and second axes X1 and X2 are orthogonal.

The optical switch comprises three mirrors: a primary mirror 30 used uplink, and two secondary mirrors 31, 32 used downlink.

Each mirror 30, 31, 32 is mounted translationally movable: each mirror is for example mounted on a support adapted to slide on a rectilinear rail parallel to an axis of displacement, between two end positions. The mirrors are preferably displaced by means of a bistable electromagnetic actuator. The advantages of such bistable electromagnetic action are short switching and substantial positioning precision.

Each mirror 30, 31, 32 comprises a reflecting surface of sufficient area for reflecting a structured image coming directly from the matrix 12 (uplink), or indirectly, after reflection onto the object to be observed (downlink). The reflecting surface of each mirror is for example oriented at 45° relative to the corresponding axis of displacement.

The primary mirror 30 is positioned both between the matrix 12 and the proximal end 51 of the first image guide 5 so that its axis of displacement coincides with the second optical axis X2.

The primary mirror 30 is positioned such that there is at least one position so-called "active" of the primary mirror 30 along its axis of displacement in which its reflecting surface cuts the first optical axis X1 and reflects all of a structured image directly coming from the matrix 12.

In an active position so-called "centered" of the primary mirror 30, the point of intersection P0 between the first and second optical axes X1 and X2 is included in the plane of the reflecting surface of this primary mirror 30.

The primary mirror 30 is further positioned such that there is at least one position of the primary mirror 30 along its axis of displacement in which its reflecting surface reflects no structured images directly coming from the matrix 12.

The acquisition system 2 comprises a first camera 21 and a second camera 22.

Each camera 21, 22 comprises an optical lens adapted to receive a structured incident image.

The first camera 21 is positioned so that the axis X3 of its lens cuts the first optical axis X1 at a point P1 located between the point P0 and the proximal opening of the first image guide 5. In the embodiment illustrated in FIG. 5, the axis X3 of the lens of the first camera 21 is orthogonal to the first optical axis X1.

The first secondary mirror 31 is positioned facing the first camera 21: the axis of displacement of this first secondary mirror 31 coincides with the axis of the lens of the first camera 21.

The first secondary mirror 31 is positioned so that there is at least one position so-called "active" of the first secondary mirror 31 along its axis of displacement in which its reflecting surface cuts the first optical axis X1 and reflects all of a structured image originating from the first image guide 5 used downlink.

In a particular active position so-called "centered" of the first secondary mirror 31, the point P1 of intersection between the optical axis X1 and the axis of displacement X3 of the first secondary mirror 31 is included in the plane of the reflecting surface of the first secondary mirror 31.

The first secondary mirror 31 is further arranged so that there is at least one position so-called "passive" of the first secondary mirror 31 along its axis of displacement in which its reflecting surface reflects no structured images coming from the proximal opening 51 of the first image guide 5.

The second camera 22 is positioned so that the axis X4 of its lens cuts the second optical axis X2 at a point P2 located between the point P0 and the proximal end 51' of the second image guide 5'. In the embodiment illustrated in FIG. 5, the axis X4 of the lens of the second camera 22 is orthogonal to the second optical axis X2.

The second secondary mirror 32 is positioned facing the second camera 22: the axis of displacement of this second secondary mirror 32 coincides with the axis X4 of the lens of the second camera 22.

The second secondary mirror 32 is positioned so that there is at least one position called "active" of the second secondary mirror 32 along its axis of displacement X4 in which its reflecting surface cuts the first optical axis X1 and reflects all of a structured image coming from the proximal opening 51' of the second image guide 5' used downlink.

In a particular active position called "centered" of the second secondary mirror 32, the point P2 of intersection between the first optical axis X1 and the axis of displacement of the second secondary mirror 32 is included in the plane of the reflecting surface of the second secondary mirror 32.

The second secondary mirror 32 is further positioned so that there is at least one position so-called "passive" of the second secondary mirror 32 along its axis of displacement in which its reflecting surface reflects no structured images coming from the proximal opening 51' of the second image guide 5'.

Optical lenses can also be arranged in the optical switch to optically conjugate the elements following in pairs: the matrix 12 and the proximal opening 51, the matrix 12 and the proximal opening 51', the camera 21 and the proximal opening 51, and the camera 22 and the proximal opening 51' (these lenses are not shown in the figures for greater clarity).

The optical switch 3 also comprises a control unit 36 adapted to control displacement of the mirrors 30, 31, 32 along their respective axes. The control unit is also adapted to activate or deactivate the generator 1 and the secondary light source 8.

The control unit 36 comprises for example one or more processors and a communications interface with each element it controls. For example, the control unit 36 is connected to each of these elements by a wired link (not shown in the figures for greater clarity).

Each processor of the control unit 36 is configured to execute instructions code generating commands which are communicated to the elements to be controlled via the communications interface.

Deactivation of the generator 1 by the control unit 36 can comprise switching off the source 10 and/or configuration of each micro-mirror of the matrix 12 in its position where it reflects light emitted by the source 10 towards an absorbent surface. By contrast, the generator 1 is considered as activated when it transmits structured light to the optical switch 3.

Deactivation of the secondary light source 8 can further be done by switching off this source 8. By contrast, the source 8 is considered as activated when it transmits light in the optical fiber 7.

Controlling Primary and Secondary Mirrors

To switch the endoscope E in its first mode (left active vision), the control unit 36 moves:

the primary mirror 30 into a passive position,
the first secondary mirror 31 into a passive position, and
the second secondary mirror 32 into an active position.

The control unit 36 also activates the generator 1 and deactivates the secondary light source 8.

Figure 7:
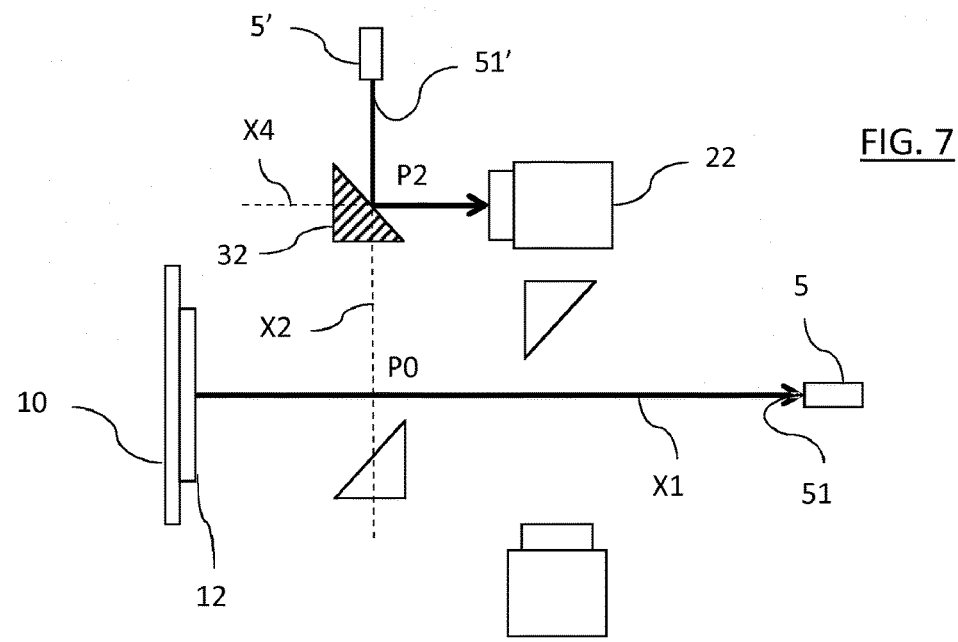
FIGS. 7 to 9 illustrate the proximal part of FIG. 6 configured respectively in first, second and third modes of the corresponding imaging device.

In the first mode illustrated in FIG. 7, the light emitted by the light source 10 is structured by the matrix 12, borders the first optical axis X1, reaches the proximal opening 51 of the first image guide 5, is conveyed by the first guide 5 uplink as far as the distal tip 6, is reflected by the object to be observed, again enters the distal tip 6 then in the second image guide 5' downlink until it reaches its proximal end 51', borders the axis X2, is reflected by the second secondary mirror 32 in active position on the axis X4, and finally reaches the lens of the second camera 22.

Also, to switch the endoscope in the second mode (right active vision), the control unit 36 moves:

the primary mirror 30 into an active position,
the first secondary mirror 31 into an active position, and
the second secondary mirror 32 into a passive position.

The control unit 36 also activates the generator 1 and deactivates the secondary light source 8, if this is not already the case.

Figure 8:
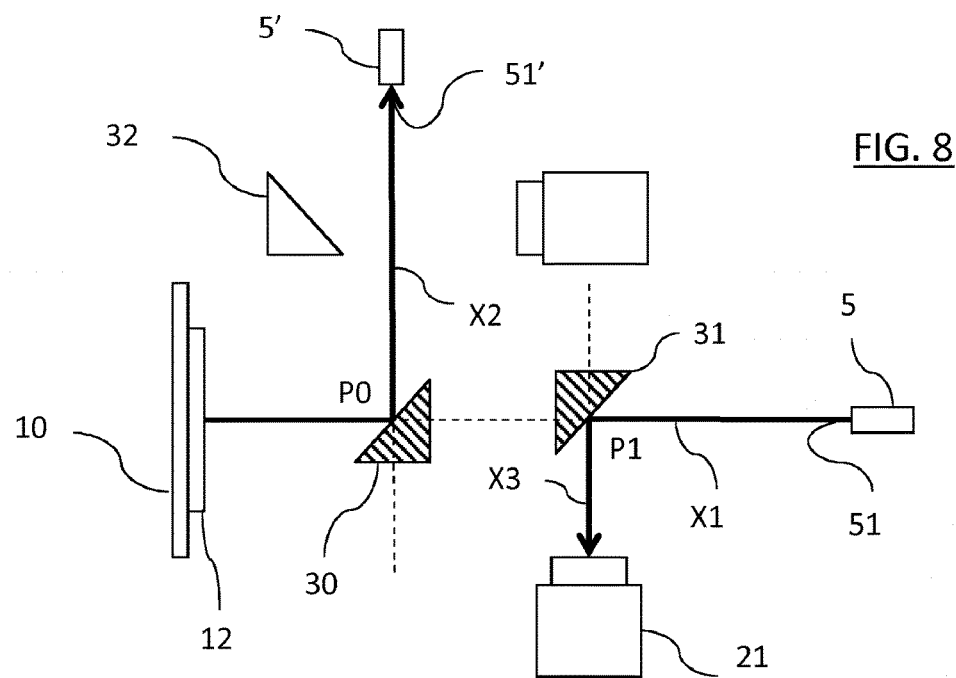

In the second mode, illustrated in FIG. 8, the light emitted by the light source 10 is structured by the matrix 12, borders the first optical axis X1, is reflected by the primary mirror 30, is redirected along the second optical axis X2, reaches the proximal opening 51' of the second image guide 5', is conveyed uplink as far as the distal tip by the guide 5', is reflected by the object to be observed, again enters the distal tip then the first image guide 5, is conveyed downlink until it reaches the proximal opening 51, borders the axis X1, is reflected by the first secondary mirror 31 in active position on the axis X3, and finally reaches the lens of the first camera 21.

Furthermore, to switch the endoscope to the third mode (passive stereovision) the control unit moves each of the two secondary mirrors 31, 32 into an active position. The control unit 36 also deactivates the generator 1 and activates the secondary light source 8.

Figure 9:
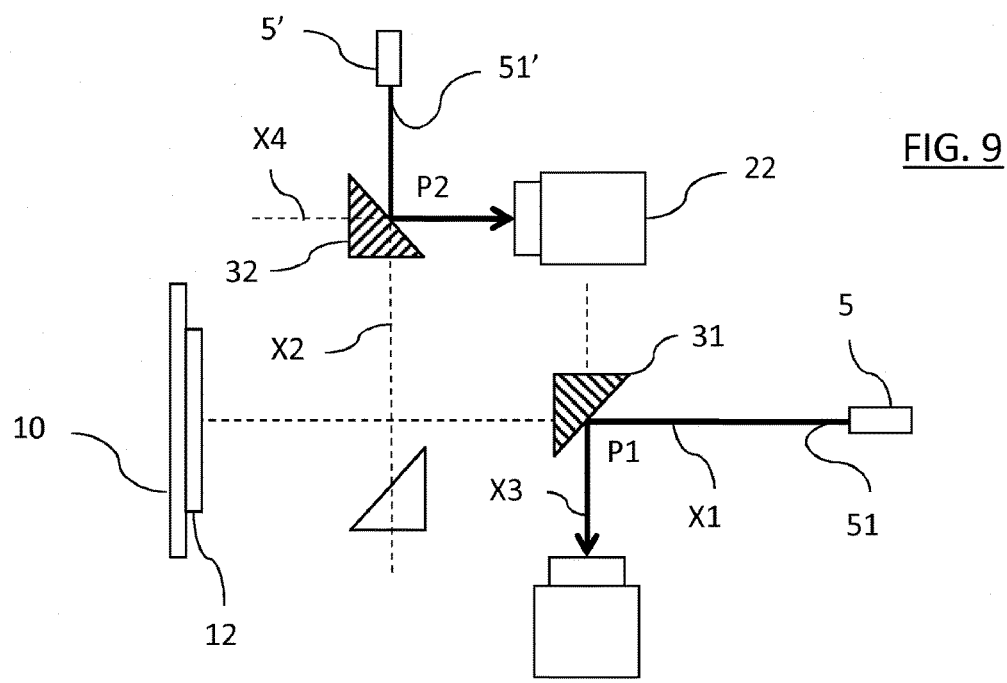

In the third mode, illustrated in FIG. 9, light generated by the secondary light source 8 spreads in the optical fiber 7 as far as the distal tip 6, leaves the endoscope by the distal tip 6 and is reflected into an area of the surface S of a three-dimensional object to be observed. The structured light reflected in this way again enters the endoscope by the distal tip 6, spreads by downlink in the two image guides 5 and 5' not used uplink, then is switched by the optical switch 3 towards the acquisition system 2. The non-structured light originating from the two image guides 5 and 5' reaches the two cameras 21, 22 after reflection on the respective reflecting surfaces of the two secondary mirrors 31 and 32.

By means of only three mirrors, the endoscope E can be operated according to the three embodiments described, each mode collecting visual information on the object observed.

To switch to each of these embodiments (for example, from one to the other) the mirrors 30, 31, 32 can be shifted simultaneously so as to shorten switching time and/or avoid unwanted configurations of the optical switch 3, such as having the primary mirror 30 and the first secondary mirror 31 simultaneously active.

Fixed lenses and diaphragms can be arranged along the axes X1 and X2 so as to focus the light beams onto a precise area. The image of 12 is formed at 51 (and not before or after 51) by way of the lenses. The image of 12 is formed at 51' also by way of the lenses. Similarly, the image of 51' is formed on the sensor of 22 by way of the lenses and the image of 51 is formed on the sensor of 21 by way of the lenses. Adding diaphragms with the lenses adjusts and improves the sharpness and/or contrast of images.

The endoscope can also comprise an image-processing unit (not shown) adapted to process images acquired by the optical acquisition system 2 and reconstruct the three-dimensional envelope of the observed object from the acquired images.

The described endoscope E can be used for any type of inspection of organs, for example for performing a colonoscopy or a laparoscopy, and for inspection of pieces in a restricted environment, for example tubular inspection, and in an industrial medium.

Also, the different parts illustrated in FIGS. 4 to 9 can be realized in an imaging device other than an endoscope, for example a device for verification of a clock mechanism.

Second Embodiment of Distal Part

Figure 10:
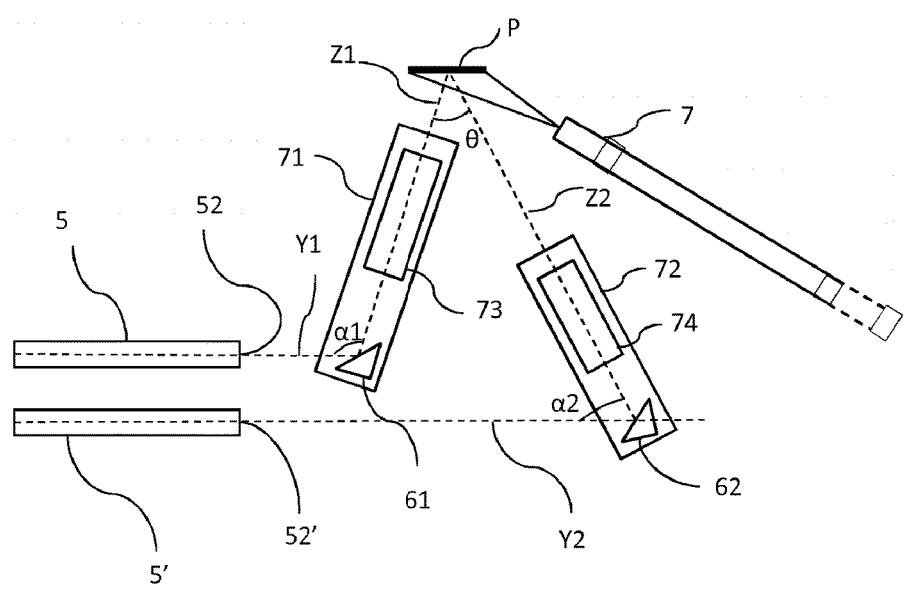
FIG. 10 illustrates the distal part of an imaging device according to a second embodiment of the invention.

A second embodiment of distal part for an imaging device will now be detailed in relation to FIG. 10.

The two image guides 5 and 5' each comprise a rigid hollow body, for example of cylindrical shape, and an array of lenses and/or mirrors arranged in this hollow body.

In the device E according to this second embodiment, further comprises two arms 71, 72.

Each arm is configured to diffuse the light conveyed by one of the image guides and redirect towards this image guide 5, 5' the light reflected by the object O.

Each arm therefore consists of a distal tip for the imaging device E according to this second embodiment.

The two arms are movable relative to each other so as to form a variable angle of reflection with the object to be observed as a function of the distance of the object relative to the two arms.

More precisely, the first arm 71 comprises a rigid hollow body having two openings: a proximal opening and a distal opening.

The proximal opening of the first arm 71 is in optical communication with the distal opening of the first image guide 5, centered on the axis Y1.

The body of the first arm 71 contains the first reflecting optical element 61, which is fixed relative to the body. The body of the first arm 71 can also comprise an optical interface such as an array of lenses 73.

The body of the first arm 71 is adapted to convey light between its proximal opening and a reflecting surface of the first reflecting element 61 along the axis Y1, and convey light between this reflecting surface and the distal opening of the body, along the optical axis Z1.

The body of the first arm 71 is mounted movable relative to the body of the first image guide 5, for example by means of an articulated link (not shown), such as a pivot link.

The optical axis Z1 in this way forms an angle α1 of variable reflection relative to the optical axis Y1, as a function of the position of the rotating arm relative to the image guide 5.

Similarly, the second arm 72 comprises a rigid hollow body having two openings: a proximal opening and a distal opening.

The proximal opening of the second arm 72 is in optical communication with the distal opening of the second image guide 5', centered on the axis Y2.

The body of the second arm 72 contains the second reflecting optical element 62, which is fixed relative to the body. The body of the second arm 72 can also comprise an optical interface such as an array of lenses 74.

The body of the second arm 72 is adapted to convey light between its proximal opening and a reflecting surface of the second reflecting element 62 along the axis Y2, and convey light between this reflecting surface and the distal opening of the body, along the optical axis Z2.

The body of the second arm 72 is mounted movable relative to the body of the second image guide 5', for example by means of an articulated link (not shown), such as a pivot link.

The optical axis Z2 in this way forms an angle α2 of variable value relative to the optical axis Y2, as a function of the position of the second arm 72 movable relative to the second image guide 5'.

For different couples of angles (α1, α2), the optical axes Z1 and Z2 of the two arms meet at a point P of variable distance relative to the arms, with an angle of reflection θ of light on a surface containing the point P, likewise variable.

Each arm can be shifted by means of a dedicated actuator (not shown in the figures), controlled by the control unit 36.

The imaging device according to the second embodiment also comprises the optical fiber 7 provided for conveying structured light or not, emitted by the secondary source 8. this optical fiber is shown here free relative to the two arms 71 and 72 and relative to the two image guides 5 and 5'.

Second Embodiment of Proximal Part

A second embodiment of proximal part for an imaging device will now be detailed in relation to FIGS. 11 to 14.

Figure 11:
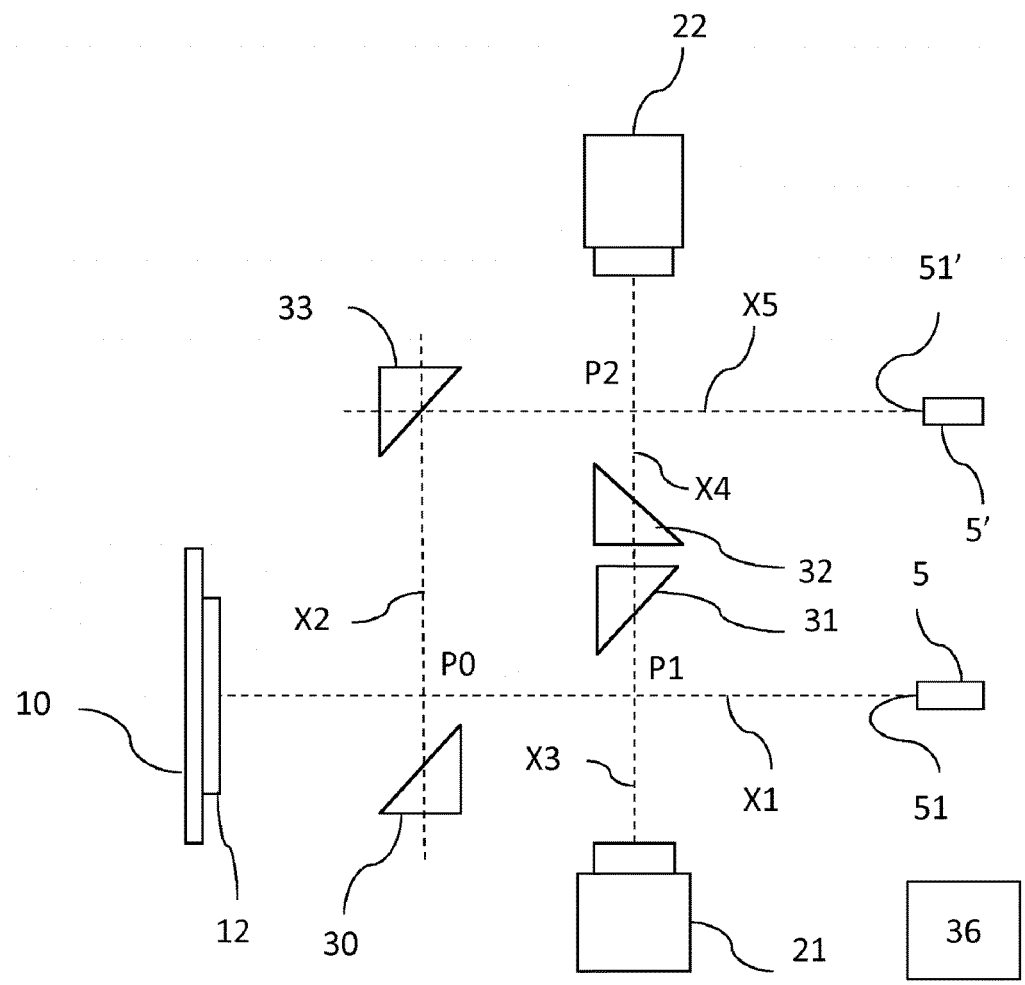
FIG. 11 partially illustrates the proximal part of an imaging device, according to an embodiment different to that shown in FIG. 6.

In reference to FIG. 11, the imaging device E according to this second embodiment takes up the following elements: the source 10, the matrix 12, the primary mirror 30, the secondary mirrors 31, 32, the two cameras 21, 22 already described.

As in the preceding embodiment illustrated, the proximal opening 51 of the first image guide 5 is centered on the first optical axis X1, facing the matrix 12, and the primary mirror 30 is arranged so as to cross the first optical axis X1 at a point P0. In the illustrated embodiment, the first and second axes X1 and X2 are orthogonal.

But this embodiment differs from that illustrated in FIGS. 6 to 9, especially as it comprises an additional fixed mirror 33.

The fixed mirror 33 is arranged on the optical path between the structured light generator and one of the two image guides, here the guide 5'.

The proximal opening 51' of the guide 5' is centered on an optical axis X5, facing the fixed mirror 33, different to the optical axis X2 and orthogonal to it.

The additional fixed mirror 33 is arranged such that its reflecting surface cuts the optical axes X2 and X5 so as to reflect all of a structured image coming from the matrix 12.

The two optical axes X1 and X5 on which the proximal openings of the two optical guides 5, 5' are centered are parallel, and both are orthogonal to the optical axis X2.

In this second embodiment, the two proximal openings of the two image guides can be positioned close to each other, which reduces the general bulk of the imaging device E. Also, placing the two image guides according to the same orientation also more simply creates the distal part (especially when it is rigid).

Also, in this second embodiment, the secondary mirror 32 is positioned so as to cut the optical axis X5 between the fixed mirror 33 and the opening 51' of the image guide 5', in its active position.

The optical axes X3 and X4 of the two cameras 21 and 22 (and displacement of the secondary mirrors 31 and 32) are combined.

Figure 12:
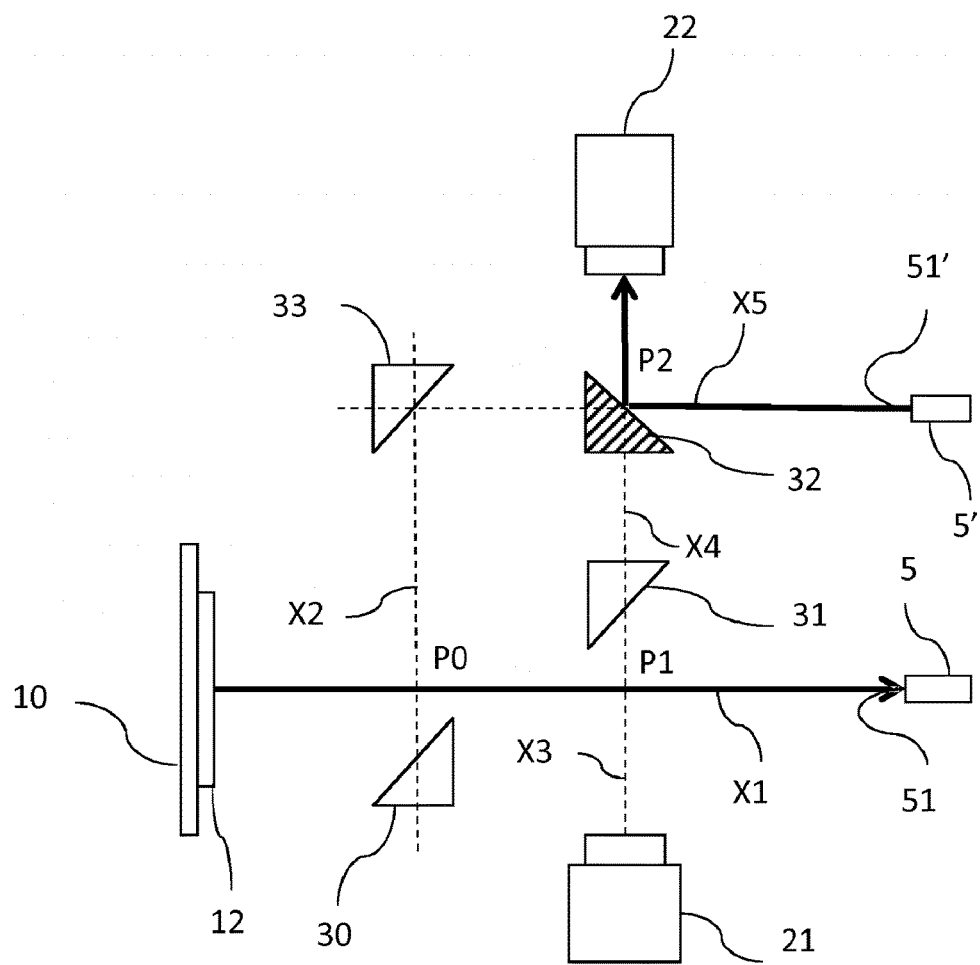
FIGS. 12 to 14 illustrate the proximal part of FIG. 11 configured respectively in first, second and third modes of the corresponding imaging device.

To configure the optical switch 3 of the device E in the first mode, the mirrors 30, 31 and 32 are shifted as per FIG. 12:

the primary mirror 30 into a passive position,
the first secondary mirror 31 into a passive position, and
the second secondary mirror 32 into an active position.

The structured light emitted by the matrix 12 borders the optical axis X1 as far as the proximal opening 51. The first guide 5 transports the structured light as far as the distal opening 51. The light enters the first arm 71, is reflected by the first reflecting element 61 and exits from the first arm by its distal opening facing the object O to be observed. After reflection onto this object O, the light enters the second arm 72, is reflected onto the second reflecting element 62, enters the second image guide 5' by its distal opening 52'. Then, this reflected light leaves the guide 5' by its proximal opening 51', borders the optical axis X5, is reflected by the mirror 32 and is acquired by the camera 22.

Figure 13:
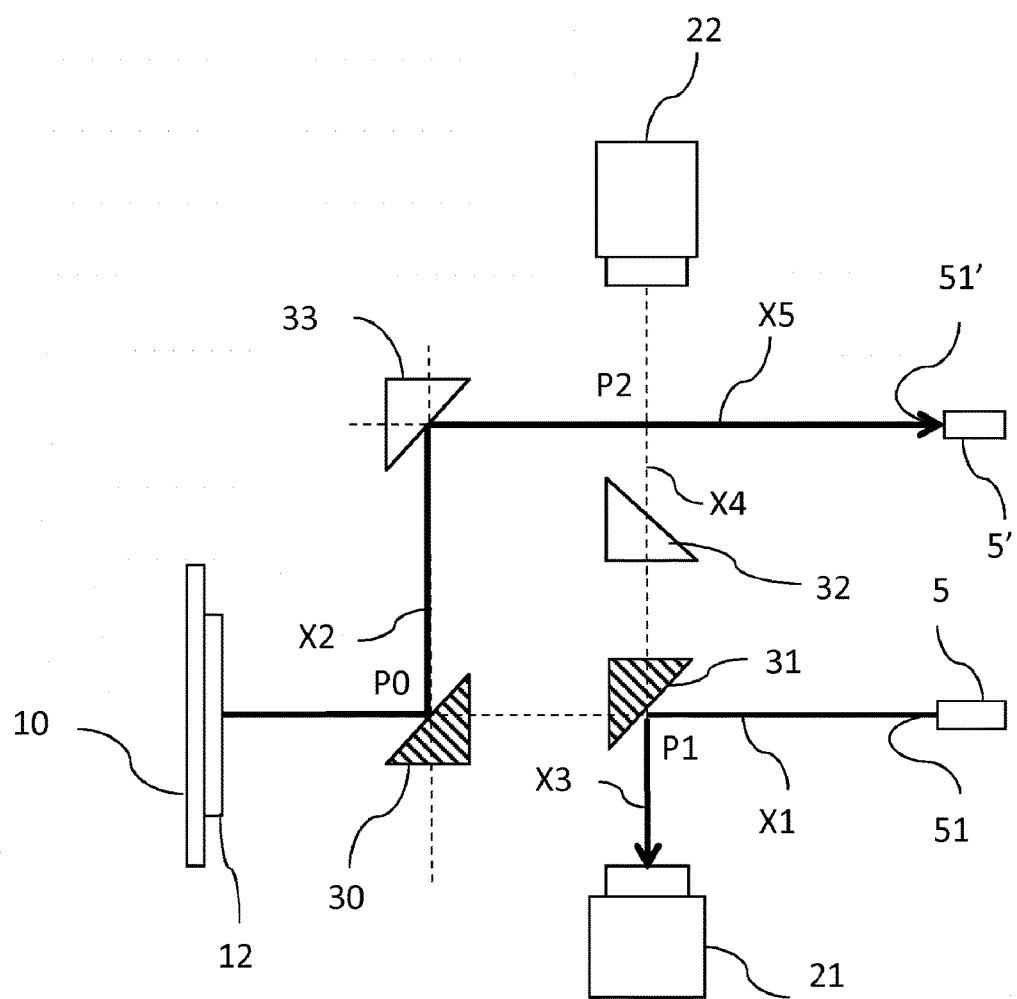

To configure the optical switch 3 of the device E in the second mode, the mirrors 30, 31 and 32 are shifted as per FIG. 13:

the primary mirror 30 in an active position,
the first secondary mirror 31 in an active position, and
the second secondary mirror 32 in a passive position.

The structured light emitted by the matrix 12 borders the optical axis X1, is reflected by the primary mirror 50 then by the fixed mirror 53, then goes as far as the proximal opening 51'. The second guide 5' transports the structured light as far as the distal opening 51'. The light enters the second arm 73, is reflected by the second reflecting element 62 and leaves the second arm by its distal opening facing the object O to be observed. After reflection on this object O, the light enters the first arm 71, is reflected on the first reflecting element 61, enters the second image guide 5 by its distal opening 52'. Then, this reflected light leaves the guide 5 by its proximal opening 51, borders the optical axis X1, is reflected by the mirror 31 and is acquired by the camera 21.

Figure 14:
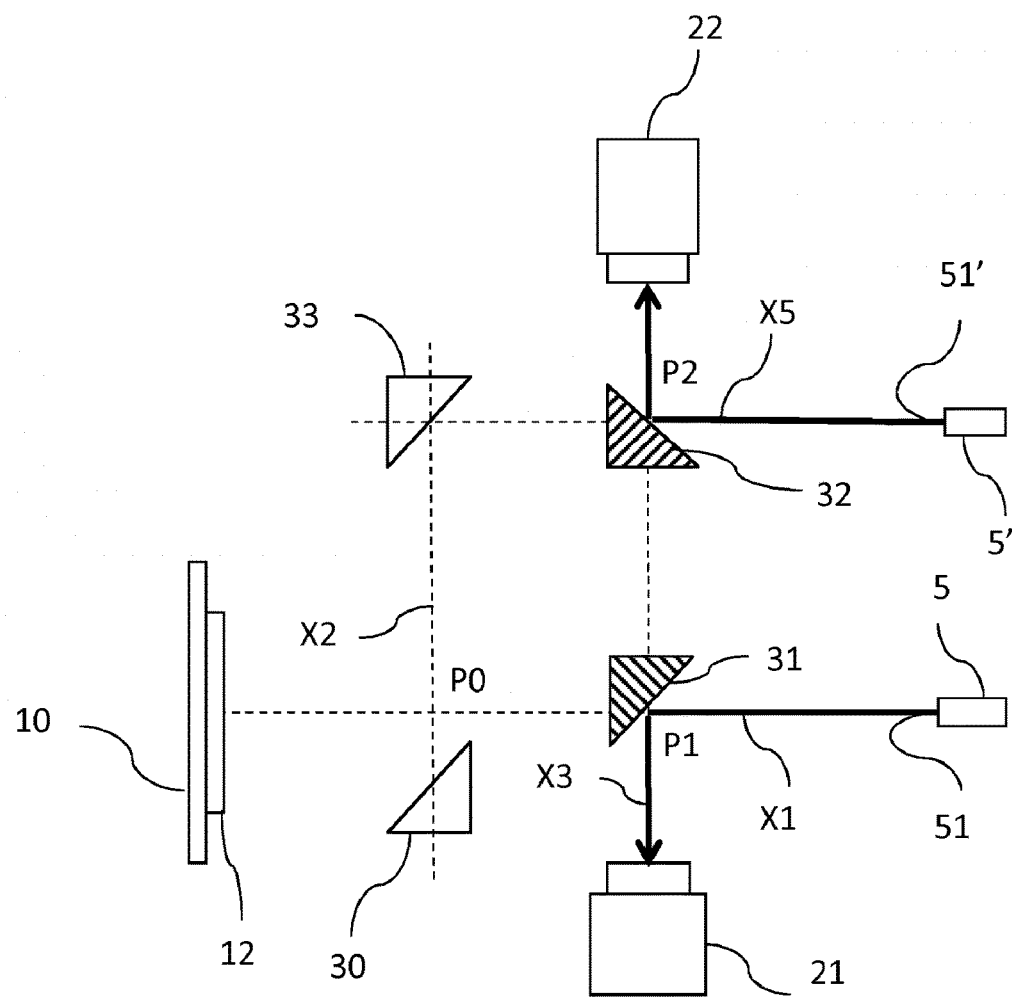

Furthermore, to switch the imaging device in the third mode (passive stereovision), the control unit 36 moves each of the two secondary mirrors 31, 32 in an active position as per FIG. 14. The control unit 36 also deactivates the generator 1 and activates the secondary light source 8.

The light generated by the light source lighting the object O is captured by each of the two arms 71, 72, guided by the two guides 5 and 5' and used as downlinks. This light reaches the cameras 21 and 22 after reflection by the secondary mirrors 31 and 32.

Other embodiments (not shown) are also possible. A non-limiting list of variants relating to one or more characteristics of the imaging device E is the following.

- The first and second optical axes X1, X2 can be secant without being orthogonal.
- The optical axes X1 and X3 can be secant without being orthogonal.
- The optical axes X2 and X4 can be secant without being orthogonal.
- The mirrors can be rotatably movable and/or be replaced by other optical elements adapted to redirect an incident light beam according to at least two alternative exit directions.
- The mirrors can be moved non-simultaneously.
- The mirrors can optionally be replaced by beam splitters or by non-actuated splitter plates.
- Other optical elements (lenses, mirrors, etc.) can be incorporated into the optical switch so as to set up more complex optical paths between the generator 1, the acquisition system 3 and the image guides 5 and 5'.
- The imaging device can comprise more than two structured image guides, at least one of the guides being stressed uplink and at least one guide being stressed in parallel downlink.
- The optical fiber and the structured image guides can be attached to the same opening O.
- The opening O can be lateral, as shown in the figures, or be made at the distal end of the tip 6.
- The number of uplinks or downlinks can be increased to exceed the value of 2, each link corresponding to a respective viewing angle of the object to be observed, so as to enrich the data of images acquired from this object.
- The number of lighting optical fibers can be increased, which passively lights at different angles and therefore modifies the problematic specular areas.
- The image guides can be inserted into the operating channels of a conventional colonoscope to enable 3D measuring and retain the usual embodiment of the conventional colonoscope.

The invention claimed is:

1. An imaging device comprising:
   at least one generator for generating a structured light,
   a first image guide,
   a second image guide,
   an acquisition system comprising a first camera and a second camera,
   an optical switch configured to switch between:
      a first mode wherein the optical switch selectively directs the structured light generated by the generator through the first image guide toward an object to be observed and selectively directs light reflected by an object then conveyed in the second image guide toward the acquisition system,
      a second mode wherein the optical switch selectively directs the structured light generated by the generator through the second image guide toward the object to be observed and selectively directs the light reflected by the object then conveyed in the first image guide toward the acquisition system, and
      a third mode wherein the optical switch simultaneously directs light coming from the first and second image guides toward the acquisition system.

2. The device according to claim 1, further comprising a secondary light source adapted to illuminate the object.

3. The device according to claim 2, further comprising an optical fiber for conveying light emitted by the secondary source towards the object.

4. The device according to claim 1, further comprising a distal tip configured to diffuse light conveyed by each of the first and second image guides on the object to be observed and redirect towards each of the first and second image guides light reflected by said object.

5. The device according to claim 1, wherein each image guide comprises a bundle of optical fibers.

6. The device according to claim 1, wherein each image guide comprises an array of mirrors and/or lenses.

7. The device according to claim 1, wherein the device is an endoscope.

8. The device according to claim 1, wherein the optical switch comprises a primary mirror positioned between the generator and the first and second image guides, the primary mirror being adapted to enable selective redirection of structured light originating from the generator towards a first optical axis leading to the first image guide or towards a second optical axis leading to the second image guide.

9. The device according to claim 8, wherein the generator is configured to emit structured light along the first axis leading to the first image guide, and the primary mirror is movable between:
   an active position in which the primary mirror cuts the first axis between the generator and the first image guide and reorients towards the second image guide the structured light originating from the generator along the second axis, and
   a passive position in which the primary mirror does not cut the first axis.

10. The device according to claim 9, further comprising another mirror arranged to redirect the light reflected by the primary mirror, when the primary mirror is positioned in its active position, on another axis parallel to the first axis, the first guide having a proximal opening aligned with the first axis, and the second guide having a proximal opening aligned with said another axis.

11. The device according to claim 9, wherein:
   the optical switch comprises a first secondary mirror and a second secondary mirror (32),
   the first secondary mirror is movable between
      an active position in which the first secondary mirror cuts the first axis between the generator and the first image guide, and reorients towards a camera light emanating from the first image guide, and
      a passive position in which the first secondary mirror does not cut the first axis,
   the second secondary mirror is movable between
      an active position in which the second secondary mirror cuts the second axis between the generator and the primary mirror, and reorients towards the acquisition system light emanating from the second image guide and a passive position in which the first secondary mirror does not cut the first axis.

12. The device according to claim 11, wherein the optical switch further comprises a control unit adapted to:

in the first mode, position the primary mirror and the first secondary mirror in a passive position and the second secondary mirror in an active position, and in the second mode, position the primary mirror and the first secondary mirror in an active position and the second secondary mirror in a passive position, in the third mode, position the secondary mirrors in an active position.

13. The device according to claim 11, wherein at least one of the primary mirror and the first and second secondary mirrors is translationally movable by means of at least one bistable electromagnetic actuator.

14. The device according to claim 1, wherein the first camera is arranged to receive light coming from the first image guide and the second camera is arranged to receive light coming from the second image guide.

15. An imaging device comprising a primary light source, a secondary light source, a first image guide comprising optical fibers extending through a shaft of the imaging device, a second image guide comprising optical fibers extending through a shaft of the imaging device, an optical fiber for conveying light emitted by the secondary light source extending through a shaft of the imaging device, an acquisition system comprising a first camera and a second camera, an optical switch configured to switch between:

a first mode for directing light from the primary light source through the first image guide toward an object to be observed and directing reflected light from the object through the second image guide toward the acquisition system, a second mode for directing light from the primary light source through the second image guide toward the object to be observed and directing reflected light from the object through the first image guide toward the acquisition system, a third mode for directing light from the secondary light source through the optical fiber toward the object and directing reflected light from the object through the first and second image guide toward the acquisition system.

* * * * *